United States Patent
Peele et al.

(10) Patent No.: US 6,792,960 B2
(45) Date of Patent: Sep. 21, 2004

(54) CLIPPER OIL STAND

(76) Inventors: Terrance Peele, 6618 Julliard Dr., Fayetteville, NC (US) 28311; Dezella M. Peele, 6618 Julliard Dr., Fayetteville, NC (US) 28311

( * ) Notice: Subject to any disclaimer, the term of this patent is extended or adjusted under 35 U.S.C. 154(b) by 93 days.

(21) Appl. No.: 10/309,019

(22) Filed: Dec. 4, 2002

(65) Prior Publication Data

US 2003/0226581 A1 Dec. 11, 2003

Related U.S. Application Data

(60) Provisional application No. 60/386,385, filed on Jun. 7, 2002.

(51) Int. Cl.[7] .............................................. B08B 3/04
(52) U.S. Cl. .................. 134/104.2; 134/116; 134/210; 30/538; 30/541; 211/70.7
(58) Field of Search ............................. 134/104.2, 109, 134/116, 135, 166 R, 170, 201; 30/1, 538, 541; 422/300, 301; 211/26, 60.1, 70.7; 248/671, 176.1, 146

(56) References Cited

U.S. PATENT DOCUMENTS

| | | | |
|---|---|---|---|
| 1,189,118 A | * | 6/1916 | Jonas .......................... 206/208 |
| 1,770,478 A | * | 7/1930 | Burnett ..................... 206/209.1 |
| 1,789,648 A | * | 1/1931 | Fowler ........................ 206/207 |
| 1,837,991 A | * | 12/1931 | Ovington .................... 211/69.6 |
| 1,843,305 A | * | 2/1932 | Sengbusch .................. 222/583 |
| 1,938,159 A | * | 12/1933 | Stewart ....................... 206/207 |
| 1,981,853 A | * | 11/1934 | Bruce .......................... 206/208 |
| 2,081,488 A | * | 5/1937 | Franz ............................. 30/36 |
| 2,095,154 A | * | 10/1937 | James ......................... 422/300 |
| 2,163,862 A | * | 6/1939 | Jack ............................ 134/137 |
| 2,313,970 A | * | 3/1943 | Roderick ...................... 451/45 |
| 2,334,191 A | * | 11/1943 | Gregory ...................... 222/577 |
| 2,336,806 A | * | 12/1943 | Hans et al. ...................... 30/41 |
| 2,349,183 A | * | 5/1944 | Mahler ........................... 422/7 |
| 2,450,816 A | * | 10/1948 | Snider .......................... 312/31 |
| 2,457,500 A | * | 12/1948 | Seandura .................... 422/300 |
| 2,462,475 A | * | 2/1949 | Di Flippo |
| 2,551,859 A | * | 5/1951 | Thompson |
| 2,662,719 A | * | 12/1953 | Hammond .................. 248/314 |
| 2,882,814 A | * | 4/1959 | Winkler et al. ............... 100/25 |
| 2,987,036 A | * | 6/1961 | Anderson ................... 118/268 |
| 3,012,109 A | * | 12/1961 | Beers ..................... 191/12.2 R |
| 3,019,494 A | * | 2/1962 | Horie et al. |
| 3,032,939 A | * | 5/1962 | Roland ....................... 451/446 |
| 3,172,416 A | | 3/1965 | Simmons |
| 3,365,267 A | * | 1/1968 | Mekiney et al. ............ 422/116 |
| 3,659,180 A | | 4/1972 | Urbush |
| 3,763,998 A | * | 10/1973 | Fisher ......................... 206/229 |
| 3,801,279 A | * | 4/1974 | Grieco ......................... 312/31 |
| 3,866,992 A | * | 2/1975 | Katz ......................... 211/69.5 |
| 3,966,408 A | * | 6/1976 | Drennen et al. ............ 422/301 |
| 4,339,876 A | * | 7/1982 | Davis .......................... 132/289 |
| 4,872,235 A | * | 10/1989 | Nielsen ................... 15/104.92 |
| 5,147,575 A | | 9/1992 | Hampton, Sr. |

(List continued on next page.)

FOREIGN PATENT DOCUMENTS

GB      2116028      *   9/1982

*Primary Examiner*—Frankie L. Stinson
(74) *Attorney, Agent, or Firm*—Richard C. Litman

(57) ABSTRACT

The clipper oil stand has a reservoir for containing a suitable oil for cleaning, lubricating, disinfecting, and scenting the blades of a hair clipper. The reservoir has at least one sidewall and a bottom wall for containing the oil, and a cover attached to the sidewall by a hinge. A well having sloped sidewalls and a perforated bottom wall depends from the cover. A sloped cradle is mounted on top of the cover. The hair clippers are placed in the cradle, blade end downwards, the clipper blades extending through an opening in the bottom of the cradle so that oil filling into the well from the reservoir cleans and lubricates the hair clipper blades.

14 Claims, 4 Drawing Sheets

U.S. PATENT DOCUMENTS

| | | |
|---|---|---|
| D339,655 S | 9/1993 | Sulik |
| 5,319,852 A * | 6/1994 | Metzger .................. 30/541 |
| 5,379,903 A * | 1/1995 | Smith ..................... 211/26 |
| D360,485 S | 7/1995 | Simonelli |
| 5,614,030 A | 3/1997 | Braun |
| 6,102,055 A * | 8/2000 | Karnatz ................... 134/88 |
| 6,257,247 B1 * | 7/2001 | Benzinger ................ 132/200 |
| 6,305,391 B1 | 10/2001 | Höser |
| 6,698,437 B2 * | 3/2004 | Hoser et al. ............ 134/104.4 |

\* cited by examiner

CLIPPER OIL STAND

CROSS-REFERENCE TO RELATED APPLICATION

This application claims the benefit of U.S. Provisional Patent Application Ser. No. 60/386,385, filed Jun. 7, 2002.

BACKGROUND OF THE INVENTION

1. Field of the Invention

The present invention relates to a devices used to hold hair clippers, and more particularly to a clipper oil stand that cleans and lubricates hair clippers while holding the clippers ready for use.

2. Description of Related Art

Hair clippers are in frequent use in barber shops, beauty salons, and other facilities where hair is cut and styled. The barber or hair stylist commonly places the hair clippers on counter tops, in recharger stands, and in holsters where they can be easily reached. During use hair, oil, grease and other contaminants tend to adhere to the cutting blades so that the blades need to be cleaned. Clipper blades also require lubrication so that the blades are freely movable, and also before sharpening. It is also considered desirable to treat the blades with a disinfectant for sanitary purposes, and it may be aesthetically pleasing to treat the blades with a perfume. A hair clipper stand which can serve each of these functions would therefore be desirable. A number of devices for performing one or more of these functions have been proposed, but none which accomplish all of these purposes.

A discussion of the present art of which the present inventor is aware, and its differences and distinctions from the present invention, is provided below.

U.S. Pat. No. 3,659,180, issued Apr. 25, 1972 to Richard L. Urbush, titled, "Self-charging Appliance and Stand" describes a cordless electric hair clipper and a recharger stand with complementary surfaces for guiding the clipper into the stand. The stand portion of the device holds the clipper horizontally and includes a trickle charger. The stand does not provide for cleaning or lubricating the clippers.

U.S. Des. Pat. No. 339,655, issued Sep. 21, 1993 to Joseph M. Sulik, titled, "Hair Trimmer and Support Base Assembly" shows an ornamental design for a stand to support a cordless hair trimmer in which the butt end or hand grip of the clippers is inserted into a support base assembly.

U.S. Des. Pat. No. 360,485, issued Jul. 18, 1995 to Robert Simonelli, titled, "Hair Clipper Stand," shows another ornamental design for a hair clipper stand. It would appear from the drawings that the butt end of the cordless clippers is inserted into the opening defined by the stand.

U.S. Pat. No. 5,147,575, issued Sep. 15, 1992 to Ronald S. Hampton, Sr., titled, "Composition and Method for Cleaning and Lubricating Hair Shears," describes an oil-based solution for cleaning and lubricating hair shears.

U.S. Pat. No. 3,172,416, issued Mar. 9, 1965 to Herbert H. Simmons, titled, "Cleaning Device for Electric Razors," describes a cleaning device for electric razors intended for shaving facial hair. The device has a motor-driven impeller for driving a cleaning fluid through a plurality of channels at high speed for cleaning the cutters of the razor.

U.S. Pat. No. 5,614,030 issued Mar. 25, 1997 to Gebhard Braun titled, "Method of Cleaning a Shaving Head of a Dry Shaving Apparatus," describes a closed circuit fluid cleaning system for electric razors. Like Simmons above, Braun does not provide a stand for hair clippers.

U.S. Pat. No. 6,305,391 issued to Jürgen Höser titled, "Cleaning Device for a Dry Shaver," describes a closed circuit fluid cleaning system for electric razors. Like Simmons and Braun above, Höser does not provide a stand for hair clippers.

None of the above inventions and patents, taken either singly or in combination, is seen to describe the instant invention as claimed.

SUMMARY OF THE INVENTION

The clipper oil stand has a reservoir for containing a suitable oil for cleaning, lubricating, disinfecting, and scenting the blades of a hair clipper. The reservoir has at least one sidewall and a bottom wall for containing the oil, and a cover attached to the sidewall by a hinge. A well having sloped sidewalls and a perforated bottom wall depends from the cover. A sloped cradle is mounted on top of the cover. The hair clippers are placed in the cradle, blade end downwards, the clipper blades extending through an opening in the bottom of the cradle so that oil filling into the well from the reservoir cleans and lubricates the hair clipper blades.

A gasket or rubber seal lines the periphery of the cover to form a seal between the cover and the sidewall(s) of the reservoir when the cover is closed. One or more latches may be provided to secure the cover in a closed position. Feet may be attached to the bottom wall of the reservoir to raise the bottom wall above a counter or tabletop, and to prevent the reservoir from sliding or skidding across a supporting surface.

The reservoir is filled with oil to a depth sufficient to raise the level of oil in the well to immerse the blades of a hair clipper placed on the stand. The clipper may be turned on for a short period, e.g., up to one minute, in order to agitate the oil and circulate the oil through the clipper blades. Hair clippings and other particulate matter washed from the blades fall through the perforations in the bottom wall of the well into the reservoir. The clippers are removed from the stand, and drained, shaken, and/or wiped to remove excess oil.

Accordingly, it is a principal object of the invention to provide a clipper oil stand for hair clippers that may be used in barber shops, hair styling salons and homes.

It is a further object of the invention to provide a clipper oil stand for supporting hair clippers in which the head of the clippers dip into a well containing oil at a depth sufficient to immerse the hair clipper blades for cleaning, lubricating, disinfecting, and/or scenting the blades.

Still another object of the invention is to provide a clipper oil stand having a cradle which supports the head end of the clippers in order to present the hand grip at the butt end of the clippers for easy manipulation by the user.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
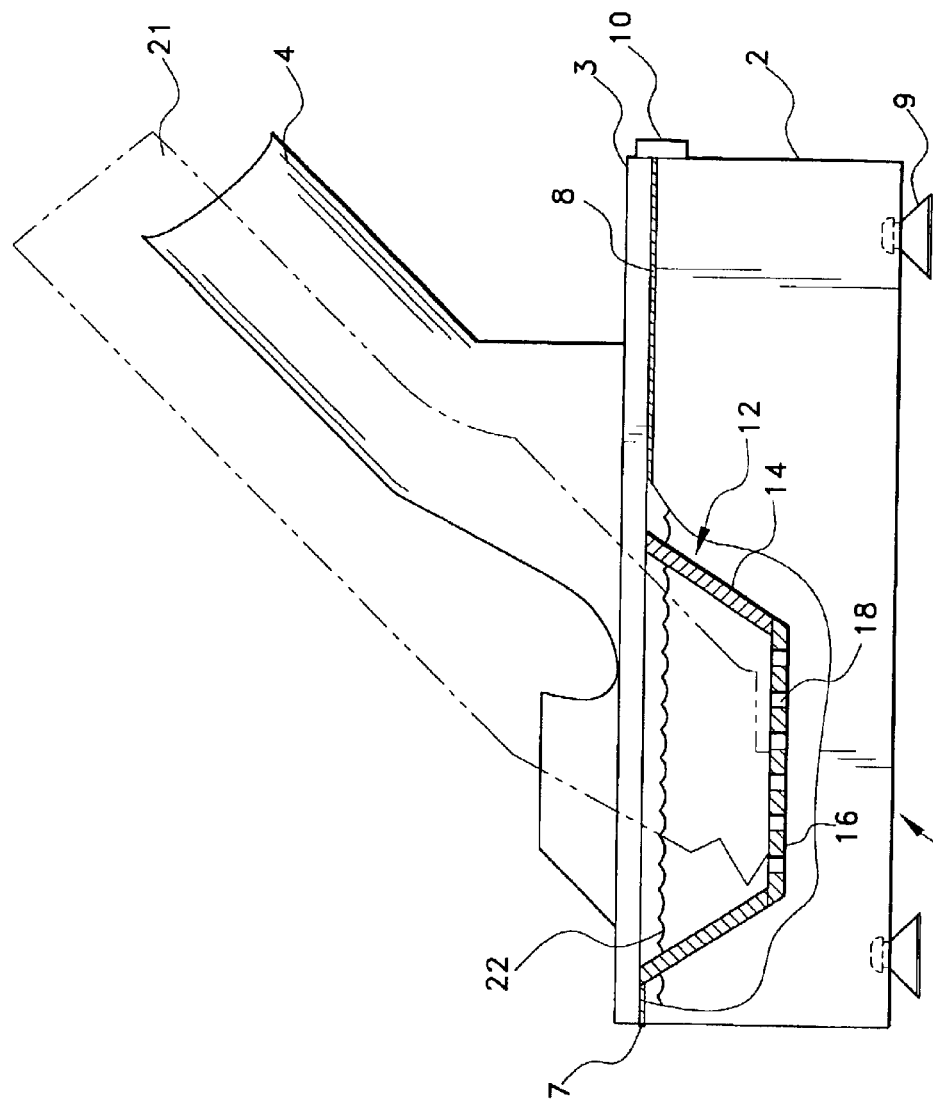
FIG. 1 is a side elevation of a clipper oil stand according to the present invention with the reservoir broken away and partly in section.

The clipper oil stand of the present invention is used to hold hair clippers, and simultaneously assists in the cleaning, lubrication, disinfection, and perfuming of the types of hair clippers commonly used in barber shops, hair salons, and homes.

FIGS. 1–4 illustrate the clipper oil stand 1 supporting a hair clipper 21, and its key components that in combination attain the desired objective, including the base oil reservoir 2, a cover portion 3, an oil seal portion 8, a cradle portion 4, and a lubricating and cleaning well portion, 12.

The reservoir 2 of the clipper oil stand 1 has a bottom wall 26 and at least one sidewall 24, and is adapted for containing a measured amount of mineral oil 22 or other liquid lubricant commonly used on human hair. The reservoir 2 is shown having a rectangular box shape in the drawings having pairs of opposed side walls and end walls, but it will be understood that the shape of the reservoir 2 is not critical, and may be circular or cylindrical, ovoid, etc. The side walls of the reservoir extend upward an equal distance to form a rim for engaging the oilproof seal 8. Suction cups or feet having a high coefficient of friction 9 are attached to the bottom wall 26 of the reservoir 2 in a plurality of locations, shown here on the corners, to prevent the accidental upsetting of the present invention from sliding or skidding across a supporting surface.

The cover 3 of the clipper stand 1 provides a platform for the cradle portion 4, a support for the lubricating and cleaning well portion 12, and a lid for the reservoir 2 of the stand 1. The cover 3 and reservoir 2 are connected with a hinge 7 shown in FIGS. 1, 2, and 3 on the front side of the reservoir 2. The hinge 7 allows for easy access to add oil to the reservoir 2 and to clean the reservoir 2 and bottom surface of the cover 3 of the clipper stand. The seal 8 is a flexible, oilproof gasket attached to and extending around the periphery of the bottom surface of the reservoir 2. With the exception of the well opening 6, the seal 8 traps the oil in the base reservoir 2 of the stand when the cover 3 is held closed by at least one latch 10. Although shown with a single latch 10 in the drawings, the clipper oil stand 1 may have a plurality of latches for securing the cover 3 in a closed position.

The well 12 is an opening defined in the cover 3, and includes one or more downward sloping sidewalls 14 depending from the cover 3 and a bottom wall 16. The bottom wall 16 has a plurality of orifices 18 defined therein so that when the cover 3 is closed, oil in the reservoir 2 enters the well 12 through the orifices 18 to a depth sufficient to immerse the blades of the hair clipper. The hair clipper may be turned on briefly (e.g., up to one minute) to agitate the oil and to circulate the oil between the blades in order to remove hairs, dirt and other particulate matter, hair oil, grease, hair creams, and other contaminants which may foul the blade, or which might be transferred from the hair and scalp of one customer to another. Hair and other particulate matter removed by such cleansing falls through the openings or orifices 18 into the reservoir 2. The well 12 may be rectangular, circular, or any other desired shape in cross-section.

Figure 2:
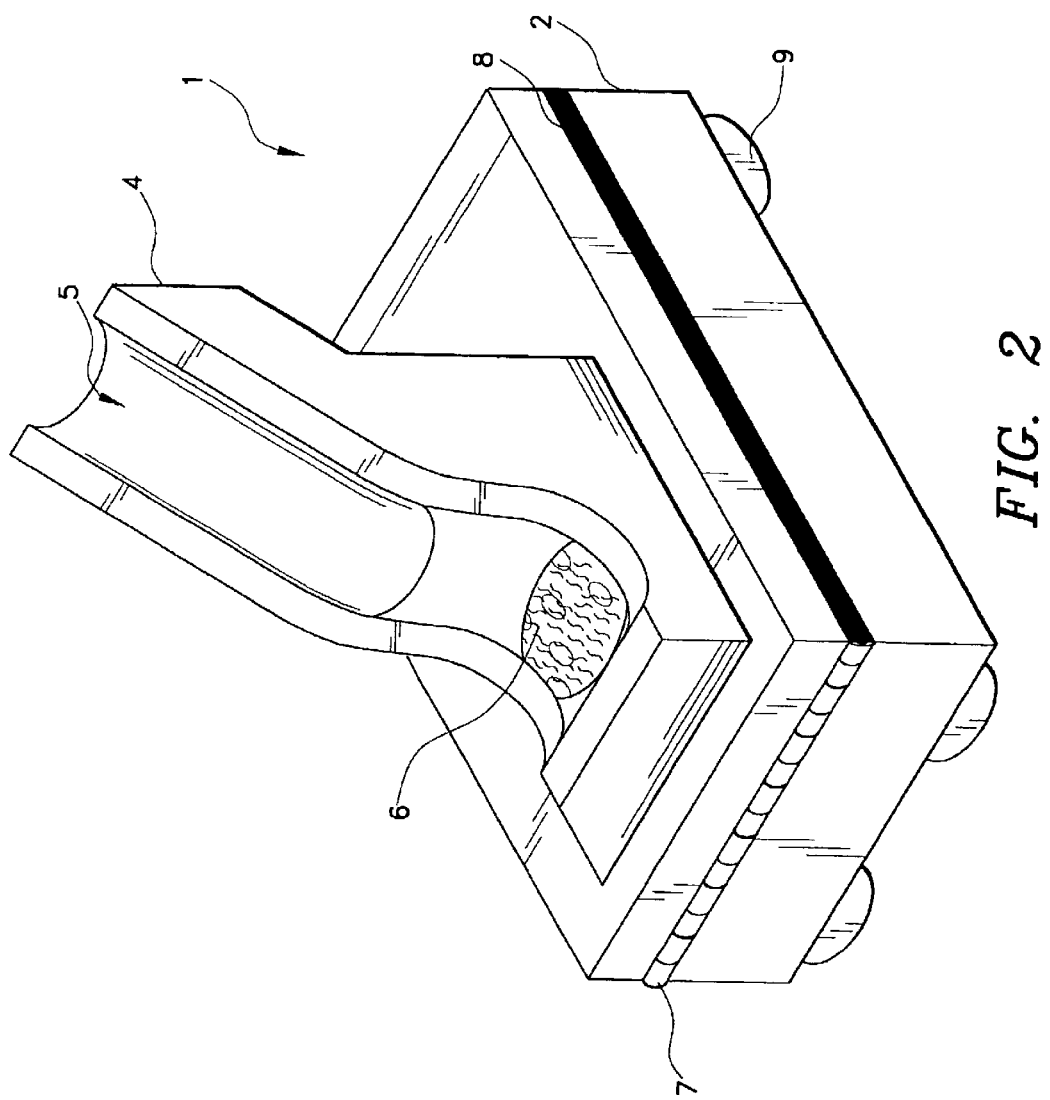
FIG. 2 is a perspective view of a clipper oil stand according to the present invention.
Figure 3:
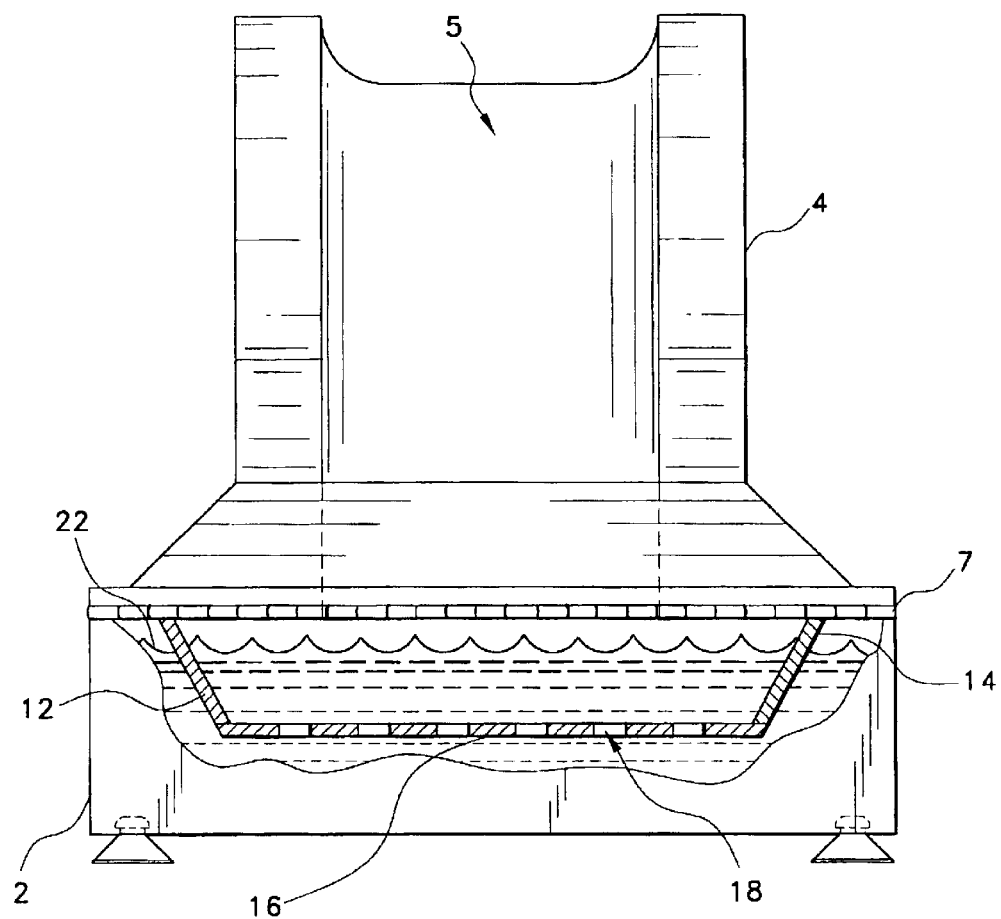
FIG. 3 is a front elevation of a clipper oil stand according to the present invention with the reservoir broken away and partly in section.
Figure 4:
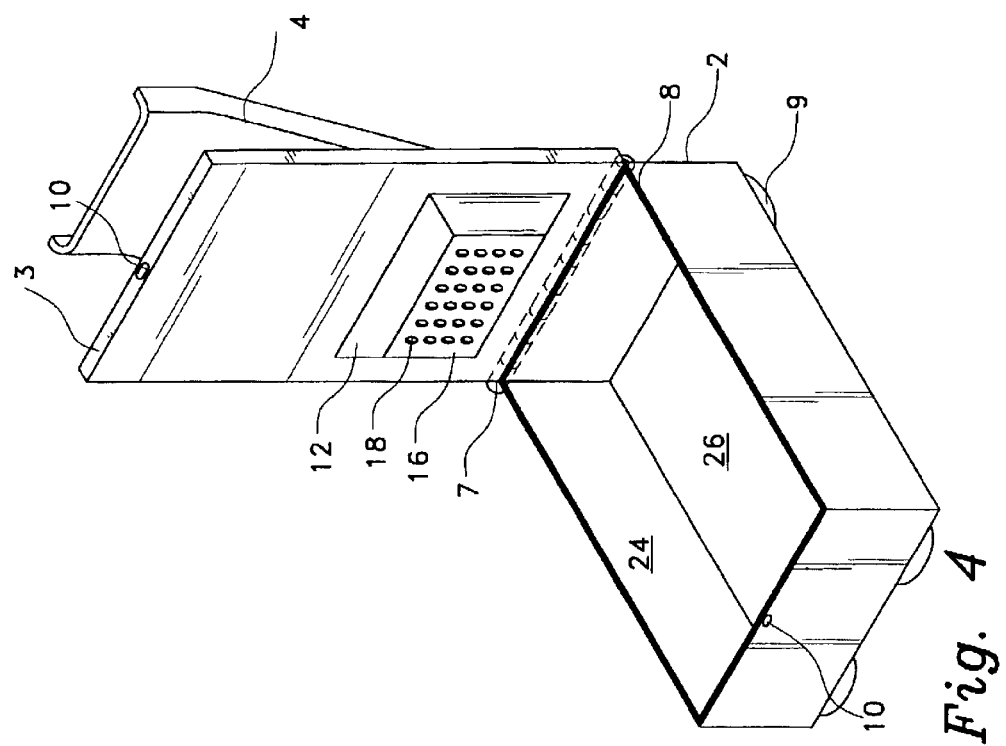
FIG. 4 is a perspective view of a clipper oil stand according to the present invention with the cover open to show details of the invention.

FIG. 2 illustrates a perspective view of the clipper oil stand 1 which clarifies the features of the cradle 4 and the cradle recess 5. The hair clipper is placed in the cradle 4 with the head of the clipper oriented downward, the handle being snugly supported by the recess 5 defined in the sloping body of the cradle 4. The cradle has an opening 6 defined in its base so that the head of the hair clipper passes through the opening 6 and into the well 12, where the head is immersed in oil, as described above. The cradle recess 5 of the present invention can be fitted with cams, shims, liners, or other devices to accommodate clippers of different sizes. Likewise, the cradle 4 can be fitted with straps, spring latches, or other fastening devices to secure the clippers 21 with the head immersed in the well 12.

The oil 22 may be any oil conventional used for cleaning and lubricating the blades of a hair clipper, and may include mineral oil, detergents, disinfectants, and may include scented material for improving the aroma of the cleaning oil. Such cleaning and lubricating oils are commercially available and well known in the art.

It is to be understood that the present invention is not limited to the sole embodiments described above, but encompasses any and all embodiments within the scope of the following claims.

We claim:

1. A clipper oil stand for supporting a hair clipper, comprising:
   a reservoir having a bottom wall and at least one side wall, said reservoir being adapted for containing an oil for cleaning and lubricating hair clipper cutting blades;
   a cover pivotally attached to the at least one side wall of said reservoir;
   a well defined by said cover, said well having at least one sidewall depending from said cover and having a bottom wall, the bottom wall of said well having a plurality of orifices defined therein; and
   a cradle mounted on top of said cover, said cradle having a recess defined therein for supporting a hair clipper and having a base with an opening defined therein, the opening being sized and dimensioned for permitting a head of a hair clipper to pass through the opening in order to immerse the hair clipper cutting blades in oil in said well.

2. The clipper oil stand of claim 1, wherein said clipper oil stand is generally rectangular in shape, said oil reservoir having a rectangular bottom wall and having mutually opposing pairs of walls extending equally upward therefrom, forming a rim.

3. The clipper oil stand of claim 2, further comprising an oilproof annular seal resting on said rim.

4. The clipper oil stand of claim 3, wherein said cover portion is rectangular in shape and sized and disposed to conform to said rectangular bottom wall and positioned above said rim and separated by said annular seal.

5. The clipper oil stand of claim 4, further comprising a hinge rotatably connecting an end of said cover portion with a corresponding end wall of said oil reservoir so as to allow rotation of said cover portion between a closed position resting on said seal of said rim and a vertically oriented upward position.

6. The clipper oil stand of claim 5, wherein said well is generally rectangular in shape having mutually opposed side walls depending therefrom and supporting said well bottom wall, said bottom wall being rectangular in shape.

7. The clipper oil stand of claim 6, wherein said mutually opposed depending side walls of said well slope mutually downwardly and inwardly from said cover portion to said well bottom wall.

8. The clipper oil stand of claim 7, wherein said well is located in a portion of said cover portion remote from said cover hinge.

9. The clipper oil stand of claim 8, wherein said cradle portion extends from an elevated position spaced generally upward from the portion of said cover portion bearing said cover hinge downward toward said cover portion defining cradle opening whereby the cutters of said hair clippers rest in said well when the clipper are placed in said cradle recess for support by said cradle portion of said cover portion of said oil clipper stand.

10. The clipper oil stand of claim 9, further comprising at latch so arranged on said oil reservoir wall and said cover portion as to maintain said cover portion in a closed and sealed position relative to said oil reservoir.

11. The clipper oil stand of claim 10, wherein there is one latch arranged on the end wall opposite that supporting said cover hinge.

12. The clipper oil stand of claim 11, further comprising a plurality of friction supports attached to and extending downward from said reservoir bottom wall for supporting said oil clipper stand in a nonslip position.

13. The clipper oil stand of claim 12, wherein said friction supports are suction cups capable of forming a sealing connection with a supporting surface.

14. The clipper oil stand of claim 2, wherein said reservoir is adapted to contain an oil having a disinfectant and a perfume.

* * * * *